United States Patent [19]

Bottka

[11] Patent Number: 5,365,334
[45] Date of Patent: Nov. 15, 1994

[54] MICRO PHOTOREFLECTANCE SEMICONDUCTOR WAFER ANALYZER

[75] Inventor: Nicholas Bottka, Burke, Va.

[73] Assignee: The United States of America as represented by the Secretary of the Navy, Washington, D.C.

[21] Appl. No.: 632,215

[22] Filed: Dec. 21, 1990

[51] Int. Cl.$^5$ .............................................. G01J 3/28
[52] U.S. Cl. .................................... 356/326; 356/328; 356/432; 356/447; 356/448; 356/445; 250/227.23
[58] Field of Search ........... 356/326, 445, 432, 432 T, 356/30, 447, 448, 328; 250/227.23

[56] References Cited

U.S. PATENT DOCUMENTS

| | | | |
|---|---|---|---|
| 4,685,801 | 8/1987 | Minekane | 356/328 |
| 4,710,030 | 12/1987 | Tauc et al. | 356/432 T |
| 4,776,695 | 10/1988 | van Pham et al. | 356/328 |
| 4,790,664 | 12/1988 | Saito et al. | 356/432 T |
| 4,922,309 | 5/1990 | Sekiwa et al. | 356/328 |

OTHER PUBLICATIONS

"Novel Contactless electroreflectance spectroscopy of semiconductors" Applied Physics Letters, 56 (6), 5 Feb. 1990; Gal et al.

Primary Examiner—Davis L. Willis
Assistant Examiner—LaCharles Keesee
Attorney, Agent, or Firm—Thomas E. McDonnell; Larry Root; Charles J. Stockstill

[57] ABSTRACT

An apparatus for measuring local carrier concentration in a preselected area of a semi-conductor is shown and described. An exciting light (preferably a laser) alters the sample's band-gap by photo injecting electron hole pairs in the area being measured. Because of the Franz-Keldysh effect, the photo injected carriers alter the sample's reflectivity. An optical fiber conducts a broad band source of probing light to the excited area on the sample. The sample reflects some of the broad band light back into a fiber that conducts the reflected light to an optical analyzer. The optical analyzer includes a dispersive element that disperses the reflected light onto a linear array of detectors. The analyzer thus simultaneously samples multiple wavelengths in the reflected spectrum. From the resulting samples, a computer deconvolutes the spectral line shape into a measurement of the local electric field and the local carrier concentration.

12 Claims, 4 Drawing Sheets

MICRO PHOTOREFLECTANCE SEMICONDUCTOR WAFER ANALYZER

BACKGROUND OF THE INVENTION

1. Field of the Invention

This invention relates to the non-destructive measurement of parameters of semi-conductor material and, more particularly, to the flaw testing of semi-conductors by measuring local carrier concentration.

2. Prior Art

The semiconductor fabrication process must carefully control parameters of the material (such as carrier concentration, electron and hole mobility, impurity content, built-in strain, heterojunction abruptness, alloy composition, and film thickness) to produce reliable devices at reasonable costs. As device yield depends upon the uniformity of these parameters over a wafer, if tests can measure these parameters over the entire wafer, bad wafers can be discarded early in the production process. This avoids processing defective wafers and, thus, allows a more cost-effective production of semiconductor devices.

Standard methods now used to evaluate wafers include Van der Paaw and polaron capacitance, microscopic, photoluminescence, secondary ion mass spectroscopic, and transmission electron microscopy. However, these methods only analyze a small section of the wafer and the methods destroy the wafer if they test more than a small section. Also, standard methods do not find end homogenities in carrier concentrations caused by imperfect crystals made early in the chip production process. While non-destructive photoreflectance techniques help overcome these drawbacks, conventional focusing means limit the areas that can be tested.

U.S. Pat. No. 4,953,983, Bottka et al, entitled *Apparatus and Method for Non-Destructively Measuring Local Carrier Concentration and Gap Energy in a Semi-Conductor*, discloses a monochromatic method for using photoreflectance and the Franz-Keldysh relationship to measure semi-conductor properties. The *Journal of Electronic Materials*, also discussed that method and apparatus in Vol. 17, page 161, 1988. In the apparatus and method disclosed in these publications, the monochrometer's aperture slit spreads the single wavelength probe over a relatively large area on the sample.

SUMMARY OF THE INVENTION

This invention relates to an apparatus for measuring local carrier concentration on a micron spatial resolution in preselected areas of a semiconductor sample. An optical fiber conducts probing light from the broadband source of light to the preselected area of the sample. A light pipe conducts monochromatic, exciting light from a laser to the preselected area on the sample. Thus, probing light from a broadband source of light and exciting light from a second source of light illuminate a preselected area of the sample. An optical fiber transmits light reflected from the semiconductor sample to a means for analyzing the sample's resulting change in reflectance.

The following detailed description of the invention and the accompanying drawings—in which like numerals denote like or similar elements—will make apparent other objects, advantages, and novel features of the invention.

DETAILED DESCRIPTION OF THE INVENTION

Figure 1:
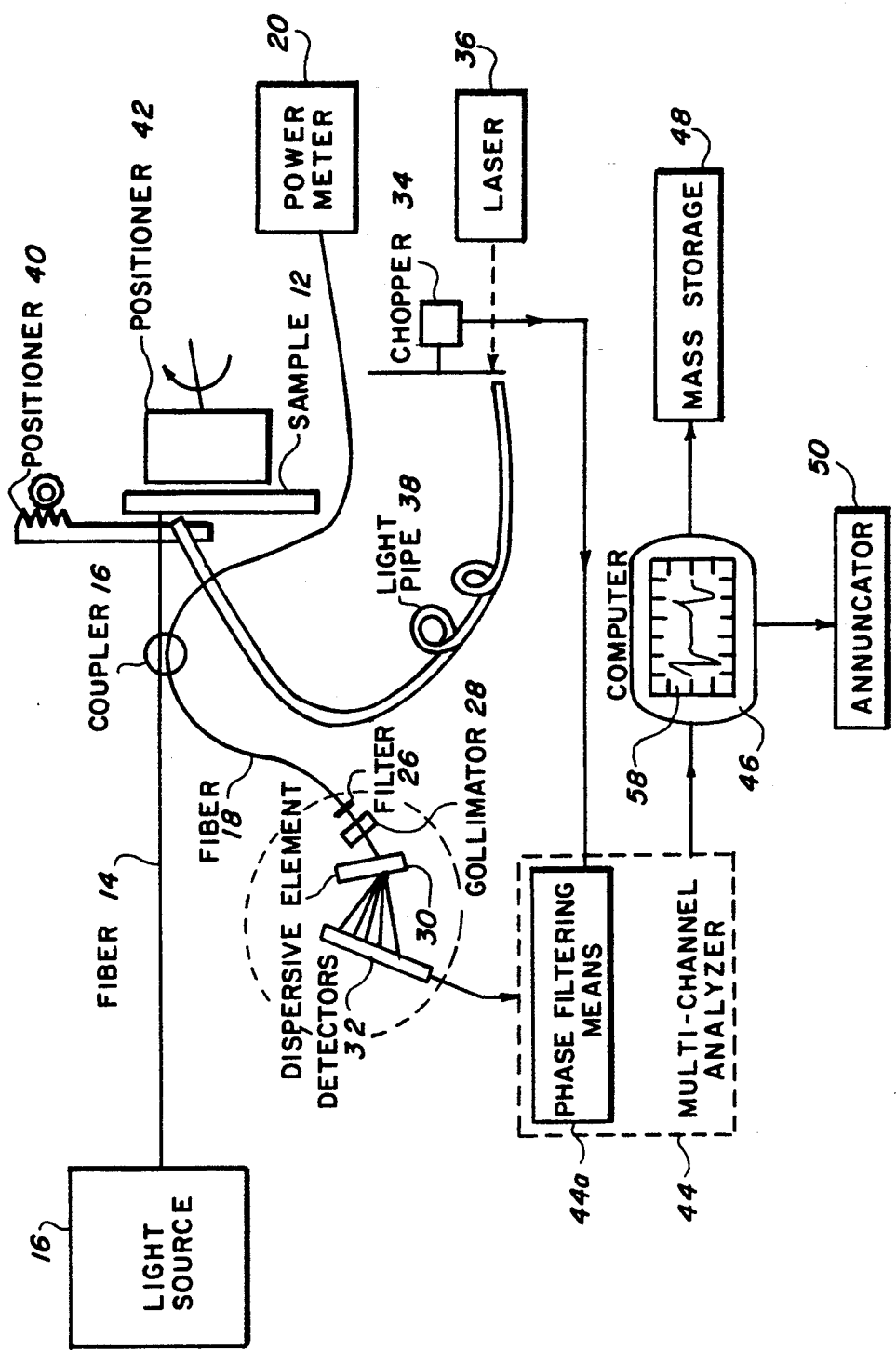
FIG. 1 is a schematic illustration of the preferred embodiment of this invention.

This invention is a method for using an improved apparatus to infer parameters of materials on a finer spatial resolution than described in the above-referenced U.S. Pat. No. 4,953,983, Bottka et al.

It is an object of this invention to infer: (a) the semiconductor carrier concentration and its variation over the wafer; (b) the semiconductor alloy composition and its variation over the wafer; (c) the built-in strain in heterostructures; and, (d) the built-in electric field at homo-junctions and heterojunctions.

It is another object of this invention to infer these parameters for small areas with a diameter of 2 microns or less.

It is another object of this invention to provide greater sensitivity, larger signal output, and, consequently, a better signal-to-noise ratio than existing methods.

It is yet another object of this invention to efficiently couple the probing light from one source to a sample while minimizing the back reflection from a second, simultaneously applied exciting light.

These and other objects are provided by the following method and apparatus.

Gallium Arsenide, Aluminum Gallium Arsenide, and other materials have a valence-conduction band-gap, $E_g$, whose conduction properties are dominated by valence to conduction band transitions at critical points. In semiconductors, this band-gap is inferred by measuring the fundamental, optical absorption edge of the material. The fundamental, optical absorptive edge shifts under the influence of an applied electric field. This shift in the absorptive edge—called the Franz-Keldysh effect—is the basis for optical characterization techniques such as electroabsorption and electroreflectance. These techniques require that the test apparatus make electric contact with the sample under test.

Photoreflectance is a contactless form of electroreflectance where periodically applied light photo-injects electron-hole pairs to modulate a built-in, surface, electric field. The photo-injected minority carriers recombine with charge in surface states thereby reducing the built-in field. This photo-injected modulation has the same type of effect on the optical constants as is produced in electroreflectance.

In the spectral line-shape relationship, the change in reflectance, $\Delta R/R$, is a periodic function described by the well known relation:

$$\frac{\Delta R}{R} = A\mathrm{Cos}\left[\frac{2}{3}\left(\frac{\hbar\omega - E_g}{\hbar\Omega}\right)^{\frac{3}{2}} - \frac{1}{4}\pi(d-1)\right]. \tag{1}$$

where A is a damping parameter; $\hbar$ is Planck's constant divided by $2\pi$; $\omega$ is $2\pi$ times the frequency of the incident light; $\Delta R/R$ is the fractional change in the reflectance, R, responsive to incident photons with energy $\hbar\omega$; $\hbar\Omega$ is the material's characteristic energy, the electro-optic parameter that accounts for the electric field and other parameters of the material; and d is the dimensionality of the critical point—for a direct gap material such as gallium arsenide at room temperature, d=3.

This relationship is a cosine oscillating in photon energy ($\hbar\omega$) rather than in time. The cosine relationship has maxima and minima—sometimes called Franz-Keldysh peaks—that occur at integer multiples of $\pi$. Thus—extracting the angle term from EQUATION 1, for the nth such peak, n=0, 1, 2, 3 ... :

$$n\pi = \frac{2}{3}\left(\frac{\hbar\omega - E_g}{\hbar\Omega}\right)^{\frac{3}{2}} - \frac{1}{4}\pi(d-1). \quad (2)$$

Quantum electromagnetic field theory teaches that the characteristic energy, $\hbar\Omega$, of a carrier particle in a local electric field is:

$$\hbar\Omega = \left[\frac{e^2\hbar^2 F^2}{8\mu}\right]^{\frac{1}{3}}; \quad (3)$$

where e is the electron charge; $\mu$ is the reduced mass of a carrier particle (electron-hole pair); and F is the local electric field strength.

For direct gap materials such as gallium arsenide, where at the fundamental absorption edge d=3, the extrema in EQUATION 1, will occur for $$[\hbar\omega]_n = (\hbar\Omega)F_n + E_g, \quad n=0,1,2,3, \quad (4)$$

Where $F_n$ is given by $$F_n = [3/2\ \pi(n+\tfrac{1}{2})]^{\tfrac{2}{3}}. \quad (5)$$

As indicated by equation 4, a plot of $(\hbar\omega)_n$ versus $F_n$ yields a straight line whose slope is proportional to the built in surface electric field of the material under study.

In materials such as gallium arsenide, the Schottky equation relates this surface electric field strength $F_s$ to local carrier concentration:

$$F_s^2 = \frac{2\ e(N_D + N_A)\left(V_B - V_P - \frac{kT}{e}\right)}{\kappa\epsilon_0}. \quad (6)$$

In the equation above, $V_B$ and $V_P$ are the built-in and photo-induced voltages in the semiconductor, respectively; k is the Boltzmann constant; T is the absolute temperature of the semiconductor; $\epsilon_0$ is the permittivity of free space; $\kappa$ is the dielectric constant of the semiconductor; and $N_D$ and $N_A$ are the ionized donor and acceptor carrier concentrations, respectively. The desired parameter, the carrier concentration, is the sum of $N_D$ and $N_A$.

If you can measure the characteristic energy, $\hbar\Omega$, the above relationships infer the local carrier concentration, $N_D+N_A$. Because the architecture of most semiconductor devices resides near the surface of the device's semiconductor wafer, the inferential measurement technique of this invention can measure the wafer's parameters that are critical to the semiconductor's architecture.

Photoreflectance measures the characteristic energy, $\hbar\omega$, of these Franz-Keldysh peaks in an area of a semiconductor. The formulas then infer the carrier concentration in that area. To take the measurement, the apparatus illuminates an area on the semiconductor with two light beams. One beam, usually a laser, excites the semiconductor by photo injecting carriers; the other beam, a broadband, or monochromatic, probing source, illuminates the semiconductor with a spectrum of light where each wavelength corresponds to a different value for $\hbar\omega$. The probing light that is reflected from the sample's surface carries the information $[R(\hbar\omega)+\Delta R(\hbar\omega)]$, where $\Delta R$ is the induced change in reflectance, R, due to changes in the surface electric field resulting from the laser-induced, photo-injected electron-hole pairs.

The apparatus measures and records the change in the sample's reflectance of light with energy $\hbar\omega$, $\Delta R$, responsive to the excitation light. The measurements identify the values of $\hbar\omega$ associated with several Franz-Keldysh peaks, n. The above equations infer the local carrier concentration, $N_D+N_A$, from the measured parameters, n and $\hbar\omega$.

Besides merely measuring the local carrier concentration, the invention can compare the measured concentration against a standard norm and identify any unacceptable deviation. With this information, the process operator can, for example, discard the entire unsatisfactory substrate.

Refer now to FIG. 1, which shows a schematic of the wafer analyzer according to this invention. Light source 10 applies a broad-band light to semiconductor sample 12 through an optical fiber 14. Coupler 16 couples some of the light in fiber 14 into fiber 18 that conducts it to optional power meter 20. Power meter 20 measures the intensity of the broadband light from source 10 so that the light's intensity can be optimized.

Fiber 14 has fire polished end 22 that forms a lens with a focal length of a few microns. End 22 focuses the light conducted through fiber 14 onto a small area on sample 12 that reflects a portion of the light back into the fiber 14. This reflected light comprises the spectrum of the light from light source 10. Optical coupler 16 couples a portion of the reflected light in fiber 14 through fiber 18 to optical analyzer 24. Optical analyzer 24 comprises a filter 26, a collimator 28, a dispersive element 30, and a linear array of optical detectors 32. In the test apparatus, dispersive element 26 was an optical grating.

Chopper 34 interrupts the light from laser 36 before the light enters light pipe 38. Light pipe 38 carries the chopped light to the same area of sample 12 that receives light from optical fiber 14. Any suitable positioning mechanism determines the position of optical fiber 14 and pipe 38. Illustrated schematically, radial positioner 40 radially moves fiber 14 and pipe 38 while rotary positioner 42 angularly positions sample 12. Radial positioner 40 and the rotary positioner 42 cooperate to select what area of sample 12 receives the light conducted by fiber 14 and pipe 38.

A multi-channel analyzer 44 receives a reference signal from chopper 34 and a data signal from optical analyzer 24 and outputs a signal to computer 46 for analysis. Mass storage device 48 stores the raw, computer input data and the analyzed results for later use. The current value of the desired parameter drives annunciator 50.

Figure 2:
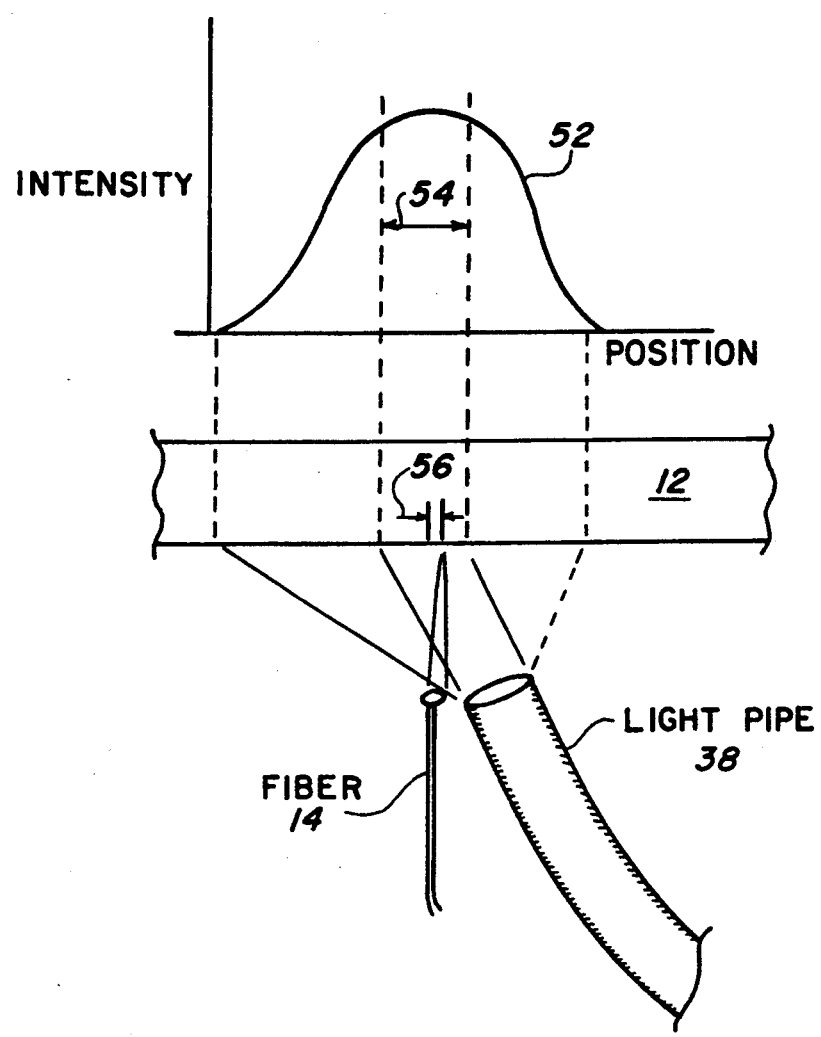
FIG. 2 is an enlarged schematic illustration showing a light pipe and an optical fiber illuminating a sample.

As shown in FIG. 2, the characteristics of light pipe 38 and fiber 14 cooperate to simplify their alignment. Light from light pipe 38 floods a relatively large area on sample 12 with an intensity that has a Gaussian distribution 52. Distribution 52 has area 54 within which the intensity is relatively uniform. In contrast, the lens formed on flame polished end 22 (FIG. 1) of fiber 14 focuses the probing light in fiber 14 into a much smaller probed area 56. Uniform area 54 is about a millimeter across while probed area 56 is less than 2 microns across. Because uniform area 54 is much larger than probed area 56, fiber 14 and light pipe 36 can be significantly misaligned without degrading the system's performance.

Referring back to FIG. 1, the invention's operation can best be understood by considering a single wavelength from the spectrum produced by light source 10. Light pipe 38 conducts the light from laser 36 to a preselected area on sample 12 where the laser light modulates the sample's reflectivity. Fiber 14 conducts the probing light from source 10 to part of the area illuminated by laser light from pipe 38. Sample 12 reflects some of the probing light from fiber 14 back into the fiber where coupler 16 transfers a portion of the reflected light to fiber 18. Filter 26 protects optical analyzer 24 by rejecting light at the wavelength emitted by laser 36. Collimator 28 then collimates the light onto dispersive element 30 that directs the wavelength of light to a single element in linear array of detectors 32. Multi-channel analyzer 44 receives the detected signal from detector 32.

At a regular frequency, chopper 34 periodically interrupts the light from laser 36 so that the laser pulses sample 12 at a predetermined rate. A reference signal from chopper 34 keys a phase filtering means 44a in the multi-channel analyzer 44 to the chopper frequency so that the analyzer only passes those signals from detector 32 that are in phase with the chopper's reference signal. A process computer 46 uses the above equations (1) through (6) to infer the desired parameters and records the data in mass storage device 48.

When operated with laser 36 turned on, the system infers the parameters of interest. Optical fiber 14 directs the output of source 10 onto the same portion of sample 12 excited by laser 36. The photons from laser 36 have sufficient energy to dislodge electrons thus generating electron-hole pairs in sample 12 thereby altering the sample's local electric field. The change in local electric field in turn changes the reflectance of sample 12 due to the Franz-Keldysh effect. Thus, laser 36 modulates the reflectivity of sample 12 which, in turn, intensity modulates the light reflected back into fiber 14. Fiber 18 conducts the intensity modulated, reflected light from coupler 16 to analyzer 24. Multi-channel analyzer 44 passes to computer 46 those signals that are in phase with the chopper, the signals representing $\Delta R$.

Preferably, rather than being monochromatic, source 10 is a broadband source of light. The process described above measures $\Delta R$ for selected wavelengths in the spectrum from source 10, that is, for light of each $\hbar \omega$ that dispersive element 30 directs to an element of linear array of detectors 32. Thus, optical analyzer 24 simultaneously measures $\Delta R$ for multiple wavelengths across the spectrum from broadband source 10. With one reading, the above procedures generate a database that relates the fractional change in reflectivity, $\Delta R/R$, to photon energy, $\hbar \omega$, for one point on sample 12. Positioners 40 and 42 can then reposition sample 12 so that the apparatus of FIG. 1 probes another spot.

Preferably, computer 46 examines the database for each spot, identifies Franz-Keldysh peaks, and identifies the peak indices n and energies $(\hbar \omega)_n$ corresponding to each peak. Preferably, computer 46 also infers the carrier concentration from the equations, peak energies, and indices n. If computer 46 determines that the carrier concentration varies by more than a predetermined threshold, annunciator 50 can signal this variance.

Curve 58 of FIG. 1 illustrates how the signals from detector 32 will vary with photon energy $(\hbar \omega)$. The spikes in curve 58 correspond to the changes of reflectance in sample 12 responsive to pulses from laser 36.

Figure 3:
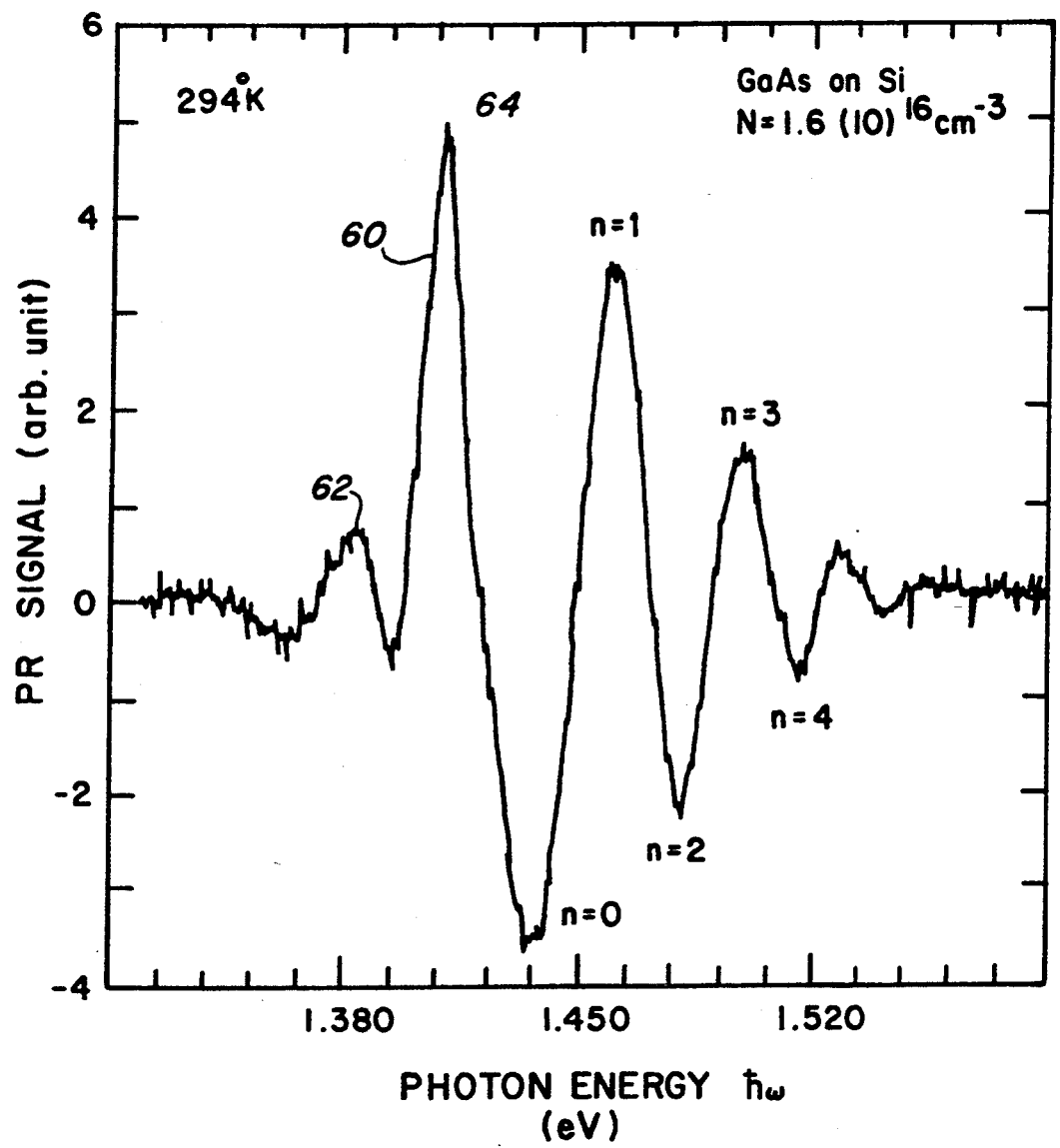
FIG. 3 illustrates Franz-Keldysh oscillations in a graph of the reflectance of a gallium arsenide sample versus the incident photon energy.

FIG. 3 shows an illustration of data taken on a gallium arsenide wafer at 294° K. The wafer was epitaxially grown on a silicon substrate, and doped to an electron carrier density of $1.6 \times 10^{16}$ per cubic centimeter. FIG. 3 shows and identifies five Franz-Keldysh peaks labeled with their corresponding peak indices n=0, 1, 2, 3 and 4. The figure shows the curve's leading edge 60 that is interrupted by the n=0 oscillation at 1.40 ev; also shown is a pseudo-peak 62 at 1.38 ev that is unrelated to Franz-Keldysh phenomena. The inventor believes that the pseudo-peak resulted from impurities in the gallium arsenide sample.

Figure 4:
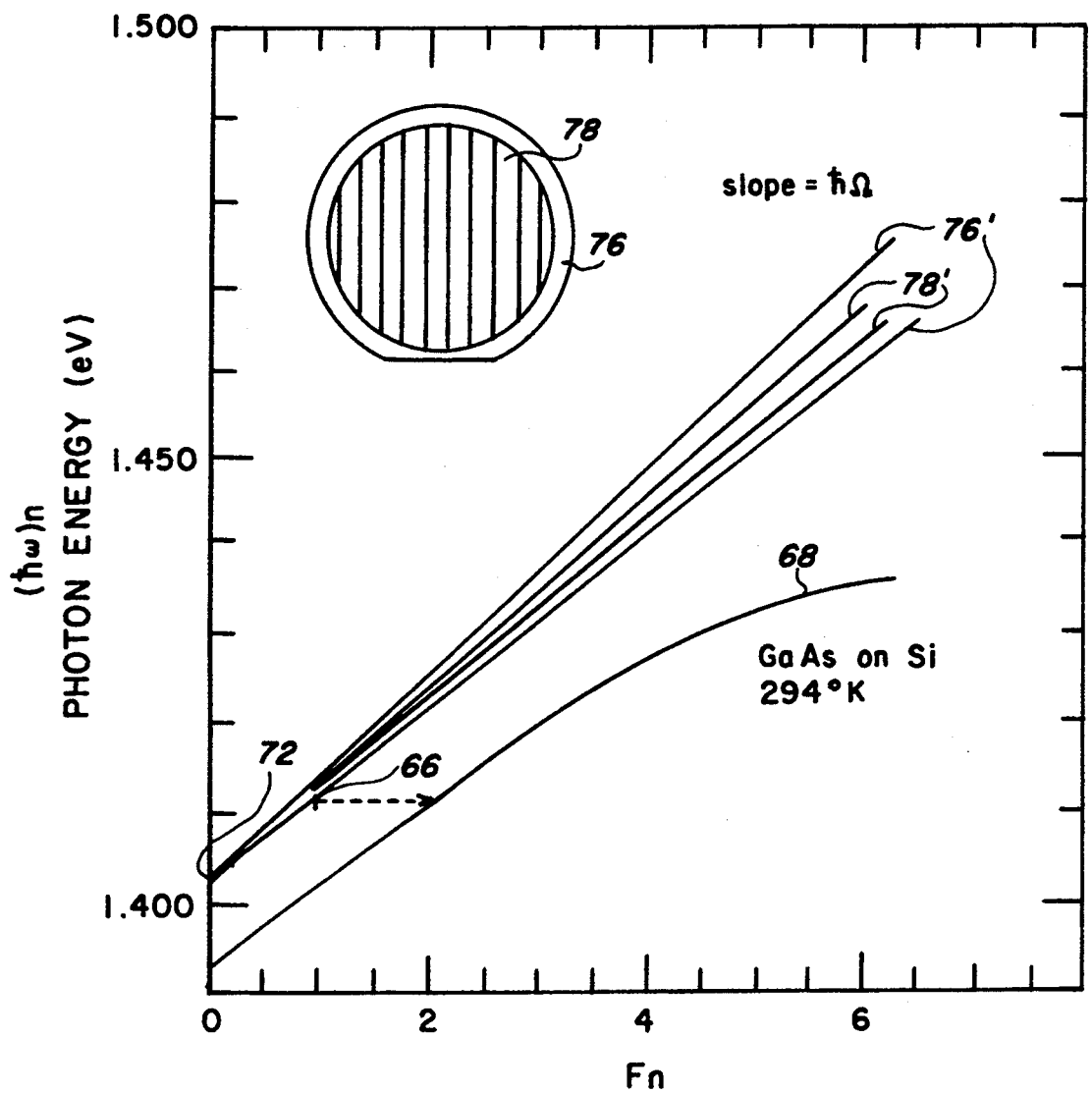
FIG. 4 illustrates a graphic method for determining the surface electric field.

As indicated by FIG. 4 and EQUATION 4, graphic plots of the energy $(\hbar \omega)$ associated with Franz-Keldysh extrema versus $F_n$ yields a straight line. The line has a slope proportional to the surface electric field—via $(\hbar \Omega)$ in EQUATION 4—and to the local carrier concentration—via EQUATIONS 3 and 6. The ordinate intercept of this plot is the material's band-gap energy, $E_g$.

FIG. 4 illustrates the graphic technique to find carrier concentration and gap energy using data taken from the same sample used in FIG. 3. Computer 46 can be programmed with a heuristic decision rule to identify the correct Franz-Keldysh index, n, associated with each peak. FIG. 4 shows the logic supporting the rule. Suppose that computer 46 initially assigns peak 64 in FIG. 3 to be Franz-Keldysh peak n=0. This causes the photon energy, $\hbar \omega$, for each true peak to be associated with an index one unit too low. The incorrect indices shift the plotted curve to the right—as shown by arrow 66—to line curve 68. Two computer testable errors show that curve 68 results from invalid assignment of the Franz-Keldysh indices.

First, the fundamental energy gap, $E_g$, is known a priori for the material under test. The energy gap for line 68, its abscissa intercept 70, is significantly below the expected energy gap, 72. This indicates both that peak 64 was improperly labeled as n=0 and that the true n=0 extrema is to the right of peak 64.

Second, the relation between $F_n$ and n is nonlinear (see EQUATION 5). Because the Franz-Keldysh indices are improperly assigned, curve 68 is not a straight line. As the hypothetical Franz-Keldysh peaks are not co-linear in the $F_n$ versus $(\hbar \omega)_n$ plot, the indices that generate curve 68 are not properly assigned.

Given these rules, computer 46 can be programmed to identify the Franz-Keldysh peaks. Once the data taken at each point on sample 12 has properly assigned indices, a group of lines such as 76' and 78' will result. Slight deviations in the lines' slopes indicate local deviations in field strength, F. The deviation in field strength varies the energy $\hbar\Omega$ associated with the Franz-Keldysh peaks. The greatest deviation occurred at locations about the sample's periphery, 76; more central portions 78 of sample 12 showed far less local deviation. Lines 76' show the greatest and least slopes measured in periphery 76; lines 78', the greatest and least slopes measured in central portion 78. Lines 76' and 78' converge near the photon energy $\hbar\omega$ axis at 1.40 ev. This intercept point is the samples's band-gap, $E_g$.

In addition to allowing visual evaluation of the curves, computer 46 could be programmed with a range of acceptable slopes for the data lines—that is, an acceptable range for characteristic energy $\hbar\Omega$. The computer could activate annunciator 50 if a resulting characteristic energy falls outside the acceptable range.

In one embodiment, light source 10 is a superluminescent diode that emits a broadband light into fiber 14. A temperature controlled heat sink (not shown) selects the operating temperature for the diode of light source 10; the temperature, in turn, controls the diode's output band width.

The grating used for dispersive element 30 may be replaced by other elements that disperse wavelengths of light, for example, a holographic grating, or a prism. Multi-channel analyzer 44 could be replaced by circuits such as a box-car integrator or a Lock-in-amplifier.

Detector 32 may comprise a linear array of 1,028 charge coupled device detectors similar to the array used in optical multichannel analyzers. Such an array will read the entire spectrum at once. Combining a broad-band light source 10 with broad band detector 32 provides a much faster response than the prior art devices that measure one optical wavelength at a time with a monochromator and a single detector. Broadband response and radial and rotary positioners, 40–42, allow this invention to measure the material's parameters significantly faster than prior devices.

The invention has been shown and described in the most practical and preferred embodiments. However, recognize that departures may be made within the scope of the invention and that obvious modifications will occur to a person skilled in the art. Accordingly, the scope of the invention is to be determined solely by reference to the appended claims.

What is claimed and desired to be secured by Letters Patent of the United States:

1. A photoreflective analyzer to measure the properties of materials for a sample, said analyzer comprising:
   a source of exciting light;
   a chopping means to periodically interrupt said exciting light;
   a first conducting means for conducting said exciting light to said sample;
   a source of broadband, probing light;
   a second conducting means for conducting said probing light to said sample;
   an optical filtering means for filtering out the wavelength of said excited light;
   a third conducting means for conducting the probing light reflected from said sample to said optical filtering means;
   a plurality of detectors for detecting the intensity of said broadband reflected probing light;
   a dispensing means for dispensing onto said plurality of detectors the wavelengths of light in the spectrum of said broadbeam reflected probing light that is passed by said filtering means; and
   a phase filtering means for isolating the changes in the detected intensities that are in phase with the frequency of said chopper.

2. The photoreflective analyzer of claim 1 wherein said second conducting means is an optical fiber.

3. The photoreflective analyzer of claim 2 wherein said fiber has a flame polished end adapted to focusing said probing light onto said sample.

4. The photoreflective analyzer of claim 1 further comprising positioner means to selectively position said sample.

5. The photoreflective analyzer of claim 1 further comprising a computer programmed to infer from the measured energy ($\hbar\omega$) and intensity: (a) the semiconductor carrier concentration and its variation over the wafer; (b) the semiconductor alloy composition and its variation over the wafer; (c) the built-in strain in heterojunctions; and, (d) the built-in electric field in homo-junctions and heterojunctions.

6. The photoreflective analyzer of claim 1 wherein said source of exciting light is a laser.

7. The photoreflective analyzer of claim 1 wherein said first conducting means is a light pipe.

8. The photoreflective analyzer of claim 1 wherein said dispersing means is a grating.

9. The photoreflective analyzer of claim 1 wherein said dispersing means is a prism.

10. The photoreflective analyzer of claim 1 wherein said dispersing means is a hologram.

11. The photoreflective analyzer of claim 1 further comprising:
   a phase filtering means for isolating the changes in the detected intensities that are in phase with the frequency of said chopper;
   a computer programmed to infer from the measured energy ($\hbar\omega$) and intensity: (a) the semiconductor carrier concentration and its variation over the wafer; (b) the semiconductor alloy composition and its variation over the wafer; (c) the built-in strain in heterojunctions; and, (d) the built-in electric field in homo-junctions and heterojunctions; and wherein
   said first conducting means is a light pipe, said second conducting means is an optical fiber with a flame polished end adapted to focusing said probing light onto said sample, said source of exciting light is a laser, and said dispersive element is selected from the group consisting of a grating, a prism, and a hologram.

12. A method for inferring (a) the semiconductor carrier concentration and its variation over the wafer; (b) the semiconductor alloy composition and its variation over the wafer; (c) the built-in strain in heterojunctions; and, (d) the built-in electric field in homo-junctions and heterojunctions of a sample of semiconductor material, said method comprising the steps of:
   a) exciting an area of the sample with an exciting light;
   b) interrupting the exciting light periodically;
   c) probing the excited area with a probing light;
   d) phase filtering the probing light reflected from the sample to remove the wavelength of the exciting light;
   e) dispensing the wavelengths in the filtered, reflected light onto a plurality of detectors;
   f) detecting the intensity of the dispersed wavelengths;

g) filtering the detected signal to isolate the changes in the reflected intensity that are in phase with said periodic interruption of the exciting light;

h) identifying the Franz-Keldysh peaks and their associated energy ($\hbar\omega$);

i) inferring the parameters from the measured values;

j) repositioning sample;

k) repeating steps a) through h) for the area of the sample at the new location;

l) repeating steps i) through j) a preselected number of times;

m) comparing the values of the inferred parameters to a preselected range of values; and n) rejecting the sample if the value of the inferred parameter is outside the preselected range of values.

* * * * *